United States Patent
Liang et al.

(10) Patent No.: US 9,758,503 B1
(45) Date of Patent: Sep. 12, 2017

(54) COUMARIN-GOSSYPOL DERIVATIVES WITH ANTITUMOR ACTIVITIES AND A METHOD OF PREPARING THE SAME

(71) Applicants: Chengyuan Liang, Xi'an (CN); Danni Tian, Xi'an (CN); Minyi Jia, Xi'an (CN); Xuechuan Wang, Xi'an (CA); Xiaolin Xie, Xi'an (CN); Dezhu Zhang, Xi'an (CN)

(72) Inventors: Chengyuan Liang, Xi'an (CN); Danni Tian, Xi'an (CN); Minyi Jia, Xi'an (CN); Xuechuan Wang, Xi'an (CA); Xiaolin Xie, Xi'an (CN); Dezhu Zhang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 15/489,711

(22) Filed: Apr. 17, 2017

(30) Foreign Application Priority Data

Mar. 27, 2017 (CN) .......................... 2017 10 185843

(51) Int. Cl.
*C07D 311/56* (2006.01)
(52) U.S. Cl.
CPC .................. *C07D 311/56* (2013.01)
(58) Field of Classification Search
CPC .................................................. C07D 311/56
USPC ....................................................... 549/248
See application file for complete search history.

(56) References Cited

U.S. PATENT DOCUMENTS

2008/0275016 A1* 11/2008 Arbiser ................ A61K 31/015
514/182

OTHER PUBLICATIONS

Baram; Chemistry of Natural Compounds, 2004, 40, 199-205.*
Tilyabaev; Russian Journal of Bioorganic Chemistry, 2010, 36, 390-395.*
Labbe-Bois; J. Med. Chem., 1975, 18, 85-90.*
Khoobi; Chem Biol Drug Des 2011, 78, 580-586.*

* cited by examiner

*Primary Examiner* — Daniel Carcanague

(57) ABSTRACT

A compound with antitumor activities is represented by formula A

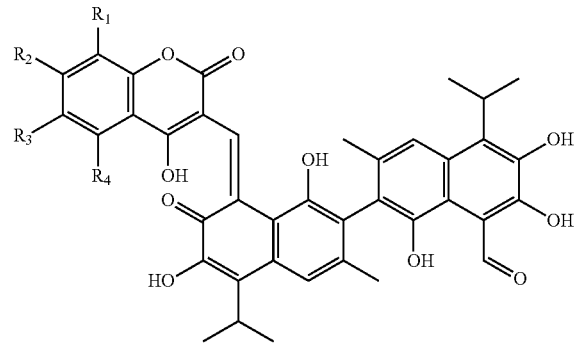

or formula B

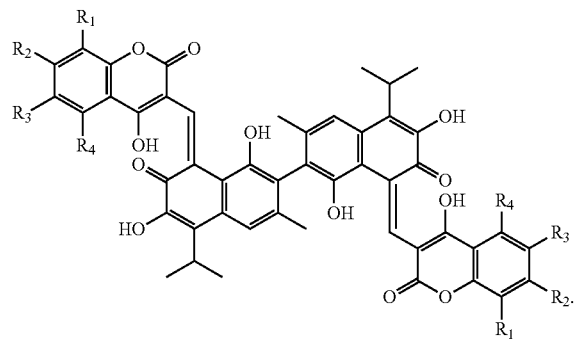

$R_1$, $R_2$, $R_3$, and $R_4$ are independently hydrogen, hydroxyl, alkoxy, halogen, formyl, unsubstituted or substituted alkyl, or unsubstituted or substituted cycloalkyl.

10 Claims, No Drawings

COUMARIN-GOSSYPOL DERIVATIVES WITH ANTITUMOR ACTIVITIES AND A METHOD OF PREPARING THE SAME

The present invention claims priority to Chinese Patent Application No. 201710185843.7, filed on Mar. 27, 2017, which is incorporated by reference for all purposes as if fully set forth herein.

BACKGROUND OF THE INVENTION

Field of the Invention

The present invention relates to the field of pharmaceutical chemistry, and in particular, to coumarin-gossypol derivatives with antitumor activities of and a method of preparing the same.

Discussion of the Related Art

Gossypol is a polyphenolic bis-naphthalene aldehyde compound, and a natural yellow pigment found in small cell glands between cotton cells. Its structure was determined in 1938. Gossypol is recognized as an effective male contraceptive agent, but at the same time it also has large toxicity. The two aldehydes in its molecule not only play a role in tautomerization but also increase its chemical activities. They may contribute to its toxicity. As a new natural product with potential, in the early 1960s, the antitumor activity of gossypol was confirmed. Studies have shown that the antitumor mechanism of gossypol relates to its ability to inhibit the activation of topoisomerase II and the stability of topoisomerase-DNA complex formation, affecting cell functions. Gossypol also activates the expression of TGF-β1 in prostate cancer cell line PC3, and inhibits cell DNA synthesis and terminates cells in G0/G1 phase. In view of its antitumor activities, in recent years, the study of anti-tumor mechanism of gossypol has become active.

Coumarin derivatives are a class of oral anticoagulant drugs. A common structure is 4-hydroxycoumarin. The core structure of coumarin derivatives is 1-benzopyran-2-one, which can be substituted with hxdroxyl, alkoxy, phenyl, isopentenyl, and other groups. Coumarin derivatives may have anti-HIV, anti-cancer, antihypertensive, antiarrhythmic, anti-osteoporosis, analgesic, asthma and antibacterial and other biological activities. They are also widely used natural spices.

Gossypol is known as male contraceptives and has been widely concerned with its excellent anti-tumor properties. Coumarin is a kind of natural organic matter which is very important in nature. It is simple in structure and high in biological activity. Therefore, the present invention utilizes the aldehyde group of gossypol and the active site of the coumarin in the coumarin structure to synthesize a kind of gossypol derivative with coumarin structure to achieve better anti-tumor activity.

Gossypol is known as male contraceptives and having some anti-tumor activities. As a nature product, coumarin has a simple structure and bioactivities.

The present invention utilizes the aldehyde group of gossypol and the active site in the coumarin structure to synthesize coumarin-gossypol derivatives to achieve better anti-tumor activities and lower toxicities.

SUMMARY OF THE INVENTION

In one embodiment, the present invention provides a compound with antitumor activities represented by formula A:

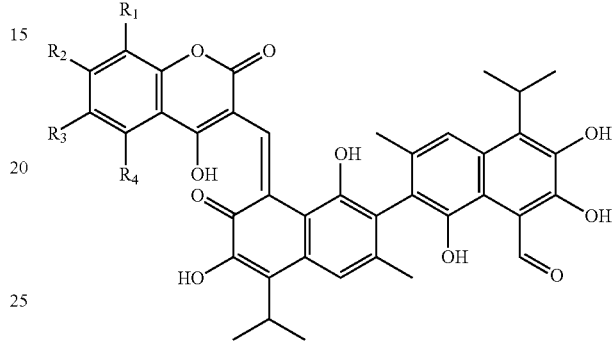

or formula B:

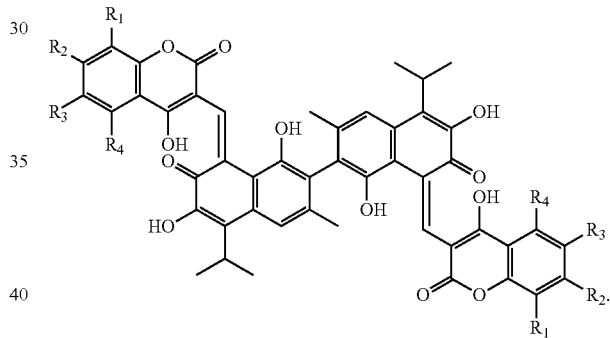

In formulas A and B, $R_1$, $R_2$, $R_3$, and $R_4$ are independently hydrogen, hydroxyl, alkoxy, halogen, formyl, unsubstituted or substituted alkyl, or unsubstituted or substituted cycloalkyl.

In another embodiment, in formulas A and B, $R_1$ is hydrogen, methoxy, hydrodroxyl, or halogen; $R_2$ is methoxy, hydroxyl, or halogen; $R_3$ is methyl, methoxy, hydroxyl, or halogen; and $R_4$ is hydrogen, formyl, hydroxyl, or halogen.

In another embodiment, the compound is:

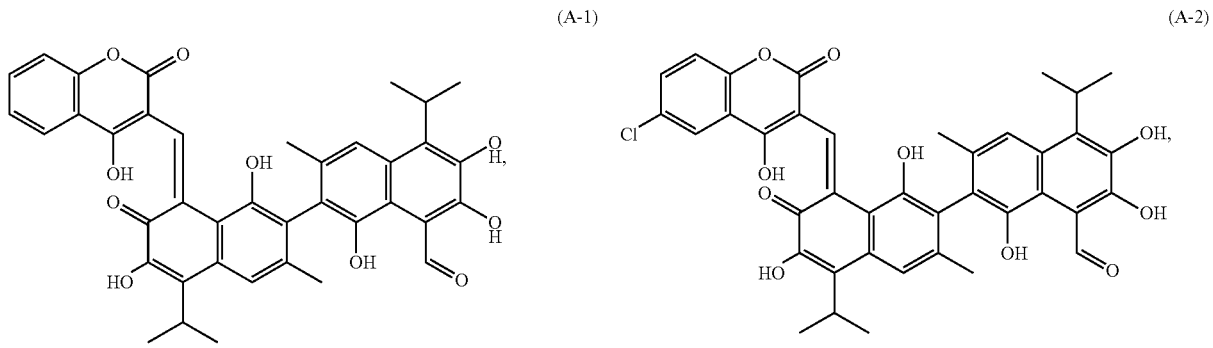

(A-1)         (A-2)

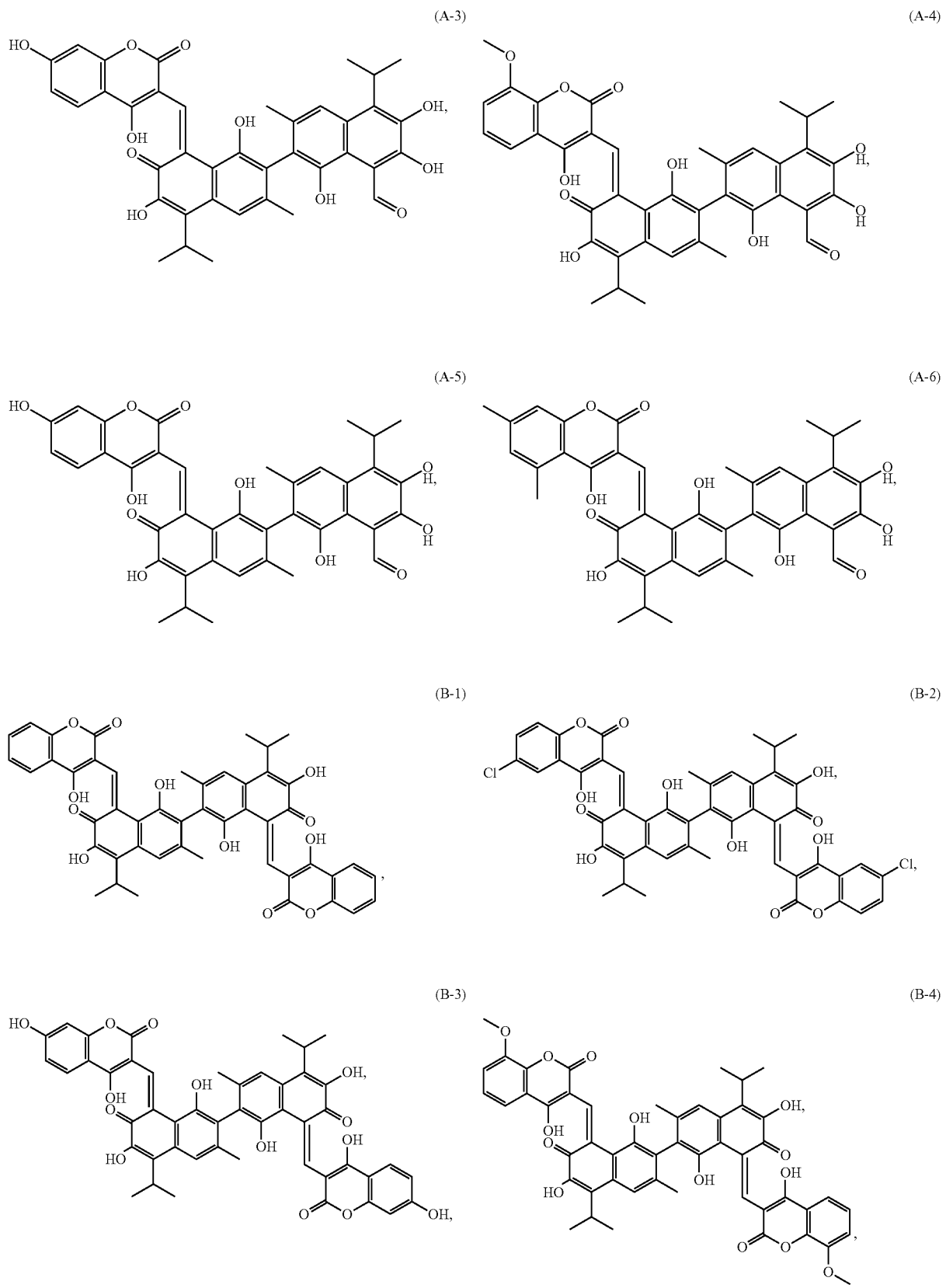

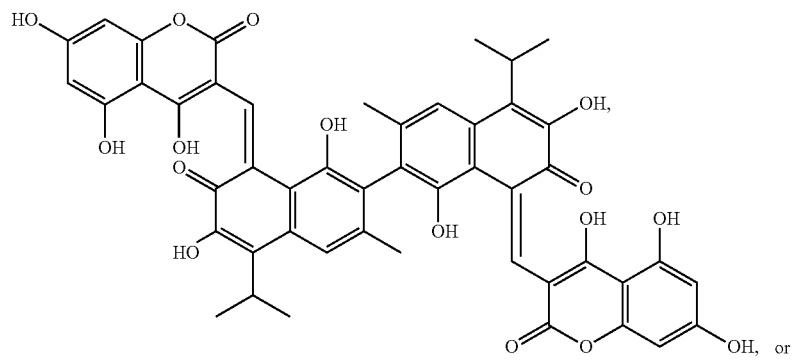
(B-5)
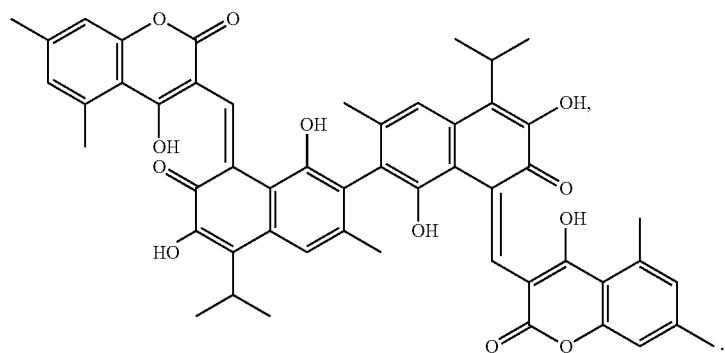
(B-6)
In yet another embodiment, the present invention provides a method of preparing the compounds described above. The method includes reacting a compound of formula C with a compound of formula D in an organic solvent with an organic base,
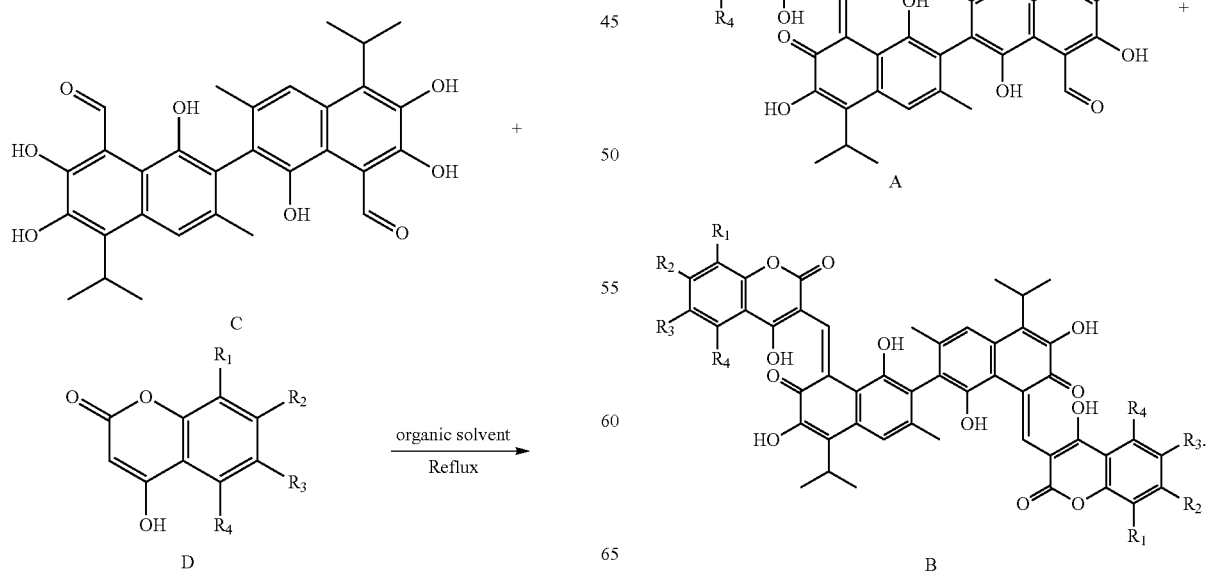

In another embodiment, the compound of formula C and the compound formula D are heated in the organic solvent for 6-9 hours.

In another embodiment, the organic solvent is acetonitrile, 1,4-dioxane, benzene, or toluene.

In another embodiment, the organic base is triethylamine, pyridine, or N-methylmorpholine.

In another embodiment, the method further includes recrystallizing the compound of formula A or formula B in methanol, ethanol, or acetonitrile.

In another embodiment, a molar ratio of the compound of formula D and the compound of formula C is 1:0.5 to 1:1.5.

In another embodiment, the molar ratio of the compound of formula D and the compound of formula C is 1:1.2.

In yet another embodiment, the present invention provides a method of using the compound in antitumor drug research, development, and application.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

As used herein, the term alkyl refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl. The term cycloalkyl refers to any monocyclic ring of an alkane having 1-8 carbon atoms. For example, cycloalkyl refers to cyclopropyl, cyclobutyl, cyclopentyl, or cyclohexyl. The alkoxy refers to an alkyl ether group wherein the alkyl moiety is as defined above.

Alkyl, cycloalkyl, and alkoxy also include saturated aliphatic hydrocarbon radicals wherein one or more hydrogens are replaced with deuterium, for example, $CD_3$.

The term halogen refers to fluorine, chlorine, bromine and iodine.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Substituents include, for example, hydroxyl, halogen, amino, nitro, alkyl, and haloalkyl. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The present invention provides coumarin-gossypol derivatives with antitumor activities and a method of preparing the same.

The structures of the coumarin-gossypol derivatives (hereafter, compounds) of the present invention are represented by formulas A and B:

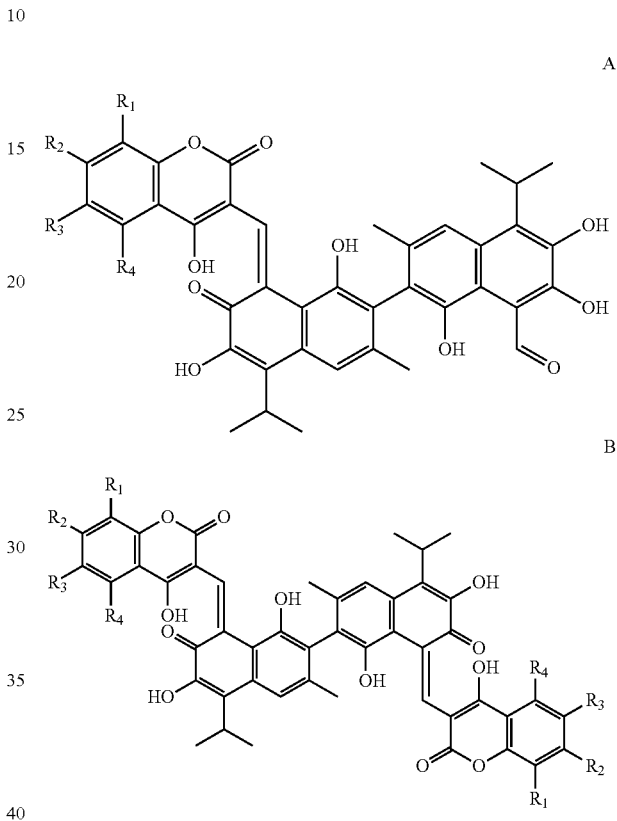

In formulas A and B, $R_1$, $R_2$, $R_3$, and $R_4$ are independently hydrogen, hydroxyl, alkoxy, halogen, formyl, unsubstituted or substituted alkyl, or unsubstituted or substituted cycloalkyl.

Preferably, $R_1$ is hydrogen, methoxy, hydrodroxyl, or halogen; $R_2$ is methoxy, hydroxyl, or halogen; $R_3$ is methyl, methoxy, hydroxyl, or halogen; and $R_4$ is hydrogen, formyl, hydroxyl, or halogen.

More preferably, the compounds have the following formulas.

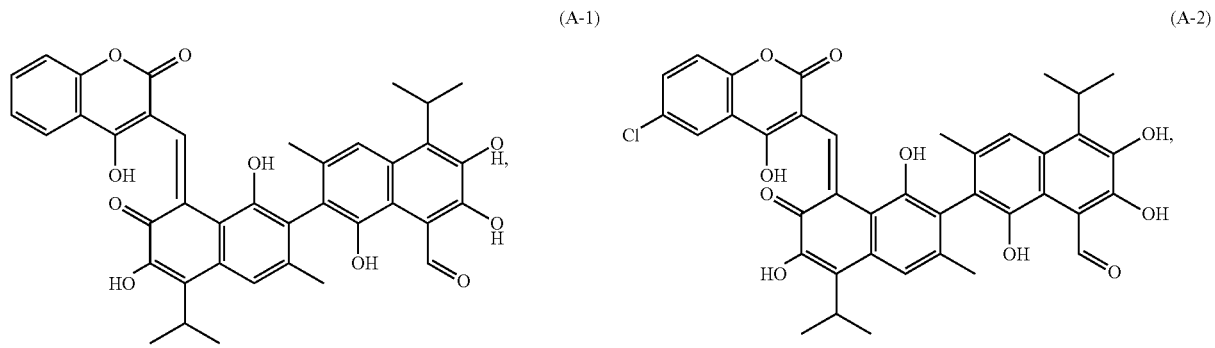

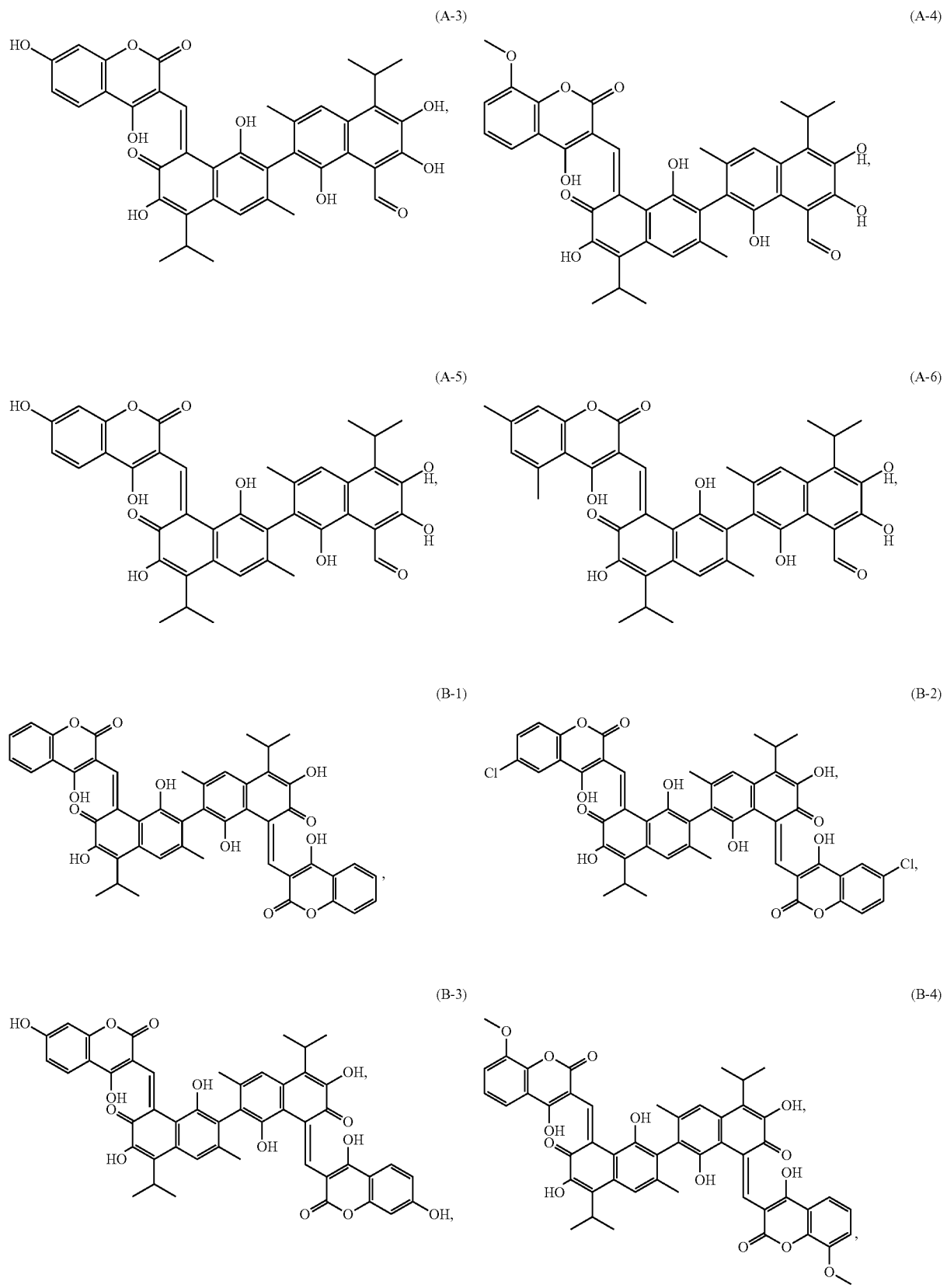

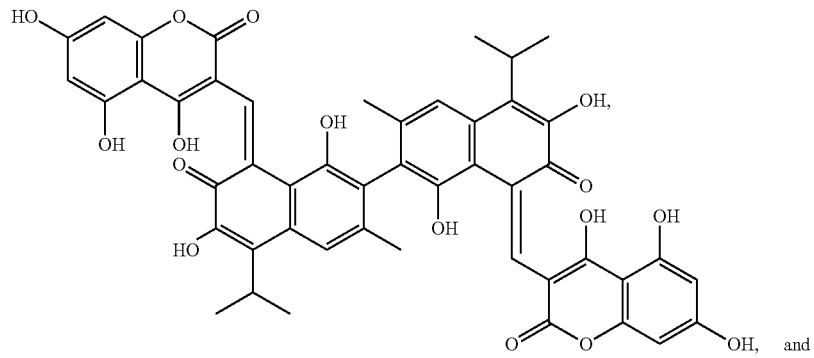

(B-5)

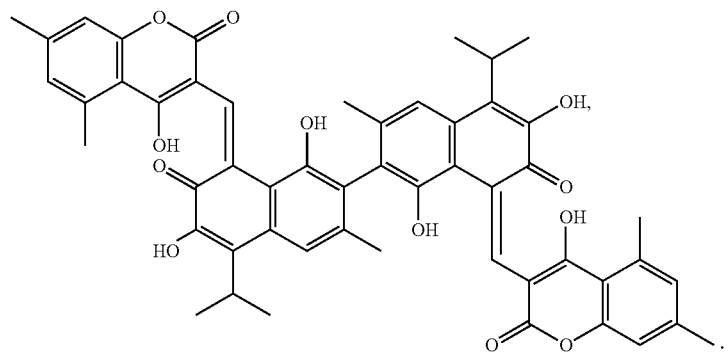

(B-6)

The present invention also provides a method of preparing the above-described compounds.

The above-described compounds are obtained by using gossypol (compound of formula C) and 4-hydroxycoumarin and its derivatives (compound of formula D) as starting materials, an organic base as a catalyst and a high boiling point organic solvent as reaction medium. The reaction products are purified by column chromatography to obtain the compounds of formulas A and B.

The synthetic route is as follows:

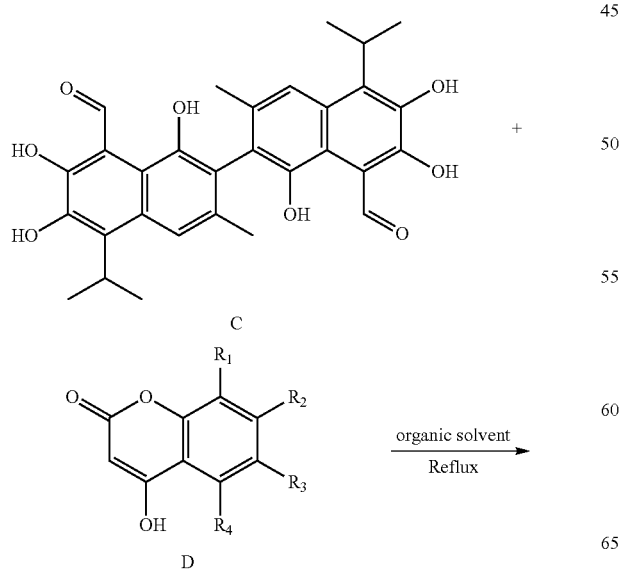

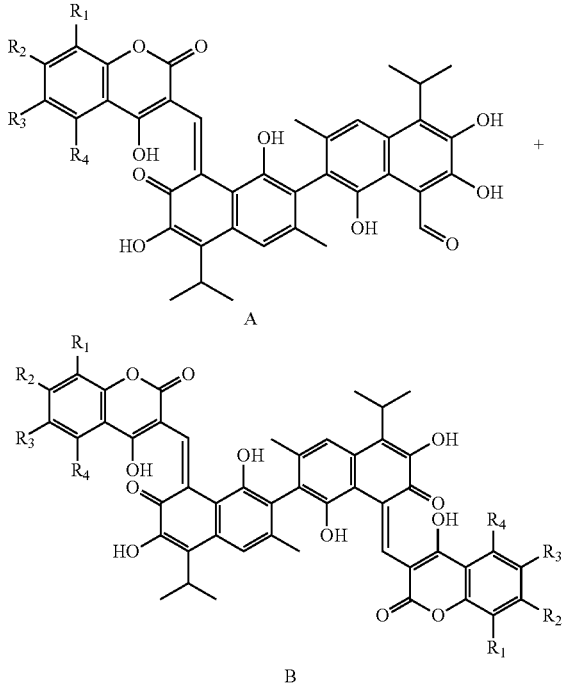

$R_1$, $R_2$, $R_3$, and $R_4$ have the same definitions as above.

The synthesis route includes the following steps.

(1) 4-Hydroxycoumarin and its derivatives and gossypol in a molar ratio of 1:0.5 to 1:1.5 were dissolved in a high boiling point organic solvent to obtain a mixture, and the mixture was placed in a round bottom flask. A fixed amount of an organic base catalyst was slowly added with magnetic stirring heated to the mixture, and the mixture was heated to reflux for 6 to 9 hours.

(2) When thin layer chromatography (TLC) indicates that the reaction is complete, stop heating, remove the condensing device. The mixture containing the crude products was concentrated under reduced pressure and purified by column chromatography.

(3) Using ethyl acetate—petroleum ether (2:1) as the eluent and TCL tracking, the eluate containing the products was collected and crystallized. The filter cake was washed with ethanol to obtain the crude products of the compounds of formulas A and B.

(4) Adding organic solvent to the crude products for recrystallization, filtering and drying to obtain target products-compounds of formulas A and B.

The organic solvent in step (1) is preferably acetonitrile, 1,4-dioxane, benzene, or toluene. More preferably, the organic solvent is toluene.

The molar ratio of 4-hydroxycoumarin and its derivative to gossypol in step (1) is 1:0.5 to 1:1.5, preferably 1:1.2.

The reaction time in step (1) is preferably 6-9 hours. More preferably, the reaction time is 8 hours.

The organic base catalyst in the above step (1) is preferably triethylamine, pyridine, N-methylmorpholine and the like. More preferably, the organic base catalyst is pyridine.

The recrystallization solvent in step (4) is preferably methanol, ethanol or acetonitrile. More preferably, the recrystallization solvent is methanol.

The invention has the advantages that the starting materials are readily available, the reaction condition is mild and safe, and the conversion rate and yield are high. The synthetic route is suitable for industrial production.

INVENTIVE EXAMPLES

The invention will now be further elucidated with reference to specific embodiments. These examples are for illustrative purposes only and are not intended to limit the scope and spirit of the invention.

Example 1

The preparation of Compound (A-1) (Z)-1,1',6,6',7-pentahydroxy-8'-((4-hydroxy-2-oxo-2H-chromen-3-yl)methylene)-5,5'-diisopropyl-3,3'-dimethyl-7'-oxo-7',8'-dihydro-[2,2'-binaphthalene]-8-carbaldehyde and Compound (B-1) (8Z,8'Z)-1,1',6,6'-tetrahydroxy-8,8'-bis((4-hydroxy-2-oxo-2H-chromen-3-yl)methylene)-5,5'-diisopropyl-3,3'-dimethyl-[2,2'-binaphthalene]-7,7'(8H,8'H)-dione is shown below.

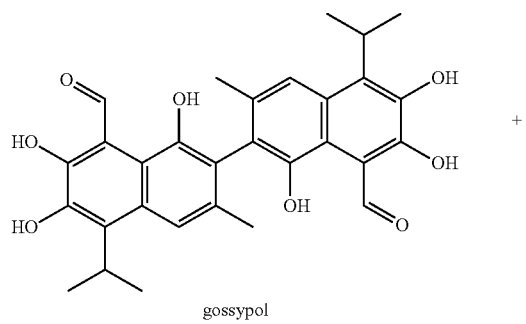
gossypol

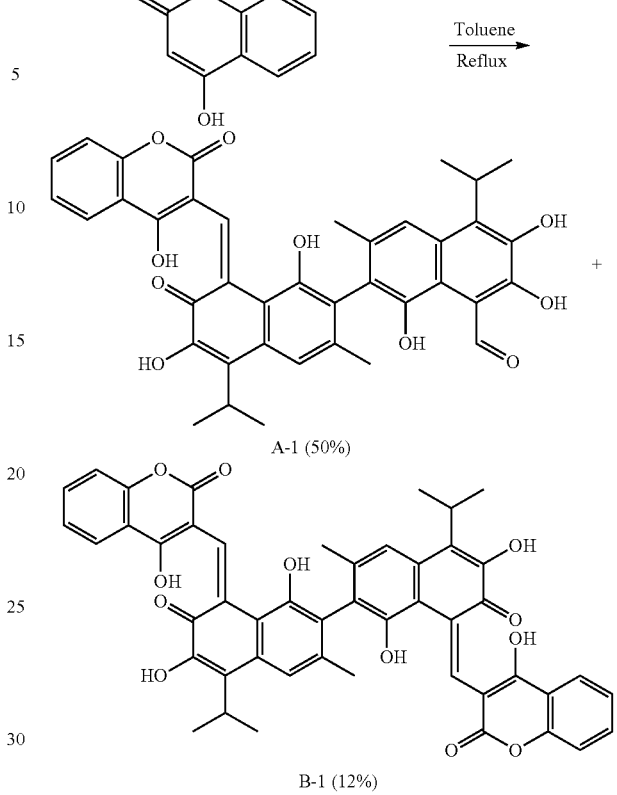
A-1 (50%)

B-1 (12%)

4.78 g (11 mmol) of 4-hydroxycoumarin and 6.2 g (12 mmol) of gossypol were dissolved in 45 mL of toluene, placed in a round bottom flask, and 2 to 3 drops of pyridine was slowly added dropwise under magnetic stirring. The mixture was then heated to 120° C. and reacted for 8 hours. When TLC indicated that the reaction was complete, reaction was stopped, the condensing unit was removed, and the reaction mixture was concentrated under reduced pressure. The concentrate was repeatedly eluted with 100 ml of eluent ethyl acetate-petroleum ether (2:1). Based on TCL tracking, the eluate containing the compound (A-1) and the compound (B-1) was collected separately. The resulting eluate was allowed to stand for crystallization and filtered, and the filtrate was recovered. The filter cake was washed with a small amount of ethanol to obtain the crude compounds (A-1) and (B-1). The crude product (A-1) was added to a reactor, and 25 ml of ethanol was added for recrystallization. After recrystallization, the resulted solution was filtered and dried to obtain 3.38 g of the compound (A-1). 0.46 g of the compound (B-1) was obtained by the same recrystallization method. The overall yield (mol %) is 62%.

Compound (A-1)

$^1$H-NMR (400 MHz, DMSO-$d_6$) δ (ppm): 12.57 (2H, s), 10.10 (1H, s), 8.30-8.98 (2H, m), 7.55-7.84 (3H, m, J=7.8 Hz, 1.3 Hz), 7.25 (1H, s), 6.83 (1H, s), 5.63 (4H, s), 2.78 (1H, m), 2.20-2.35 (4H, m), 1.98 (3H, s), 1.76 (6H, d, J=6.8 Hz), 1.41 (6H, d, J=6.8 Hz); $^{13}$C-NMR (101 MHz, DMSO-$d_6$) δ (ppm): 190.2, 178.6, 172.3, 165.6, 161.4, 157.9, 154.7, 153.4, 145.0, 142.6, 139.8, 137.2, 135.4, 133.1, 132.6, 127.3, 125.4, 123.8, 123.3, 119.6, 117.1, 116.3, 115.7, 112.6, 109.5, 90.7, 39.8, 38.4, 37.1, 30.8, 26.1, 21.3, 20.9; MS (ESI) for (M+H)$^+$: 663.2.

Compound (B-1)

$^1$H-NMR (400 MHz, DMSO-d$_6$) δ (ppm): 12.57 (4H, s), 8.64 (2H, d, J=7.5 Hz), 7.51-7.68 (6H, m, J=7.5 Hz), 7.31 (2H, s), 6.76 (2H, s), 5.65 (2H, s), 2.57 (6H, s), 2.48 (2H, m, J=6.8 Hz), 1.36 (12H, d, J=6.8 Hz); $^{13}$C-NMR (101 MHz, DMSO-d$_6$) δ (ppm): 177.8, 171.4, 160.8, 158.2, 157.4, 151.5, 141.4, 136.9, 136.2, 133.4, 127.3, 125.8, 125.4, 124.8, 123.3, 118.3, 117.3, 114.6, 104.2, 25.9, 22.8, 20.1; MS (ESI) for (M+H)$^+$: 807.2.

Example 2

The preparation of Compound (A-2) (Z)-8'-((6-chloro-4-hydroxy-2-oxo-2H-chromen-3-yl)methylene)-1,1',6,6',7-pentahydroxy-5,5'-diisopropyl-3,3'-dimethyl-7'-oxo-7',8'-dihydro-[2,2'-binaphthalene]-8-carbaldehyde and Compound (B-2) (8Z,8'Z)-8,8'-bis((6-chloro-4-hydroxy-2-oxo-2H-chromen-3-yl)methylene)-1,1',6,6'-tetrahydroxy-5,5'-diisopropyl-3,3'-dimethyl-[2,2'-binaphthalene]-7,7'(8H,8'H)-dione is shown below.

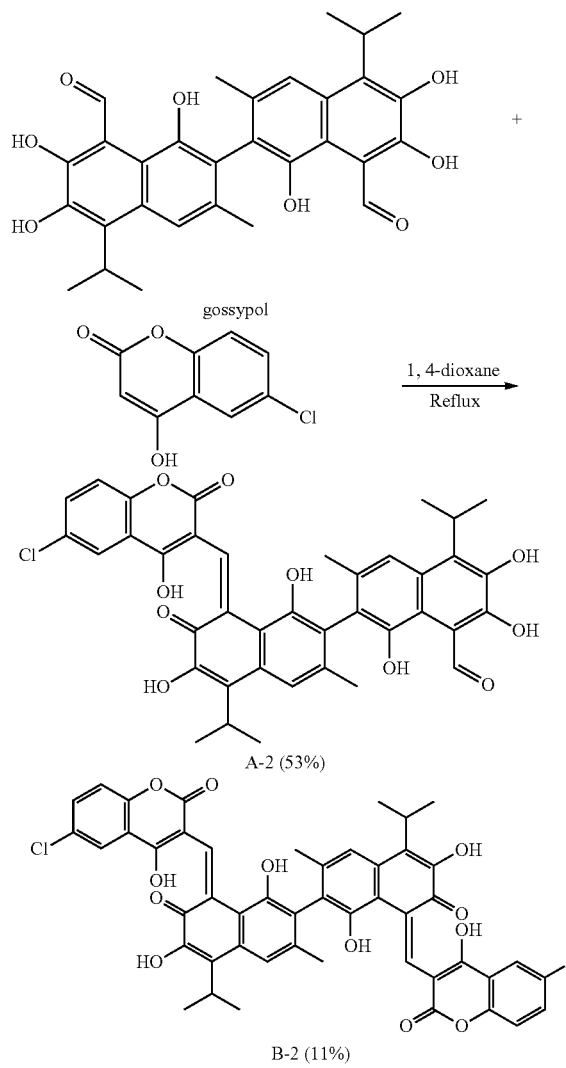

1.57 g (8 mmol) of 6-chloro-4-hydroxycoumarin and 4.67 g (9 mmol) of gossypol were dissolved in 50 mL of 1,4-dioxane, placed in a round bottom flask, and 2 to 3 drops of triethylamine was slowly added dropwise under magnetic stirring. The mixture was then heated to 110° C. and reacted for 7 hours. When TLC indicated that the reaction was complete, reaction was stopped, the condensing unit was removed, and the reaction mixture was concentrated under reduced pressure. The concentrate was repeatedly eluted with 500 ml of eluent ethyl acetate-petroleum ether (2:1). Based on TCL tracking, the eluate containing the compound (A-2) and the compound (B-2) was collected separately. The resulting eluate was allowed to stand for crystallization and filtered, and the filtrate was recovered. The filter cake was washed with a small amount of ethanol to obtain the crude compounds (A-2) and (B-2). The crude product (A-1) was added to a reactor, and 30 ml of methanol was added for recrystallization. After recrystallization, the resulted solution was filtered and dried to obtain 1.58 g of the compound (A-1). 0.32 g of the compound (B-2) was obtained by the same recrystallization method. The overall yield (mol %) is 64%.

Compound (A-2)

$^1$H-NMR (400 MHz, DMSO-d$_6$) δ (ppm): 12.61 (2H, s), 10.13 (1H, s), 9.02 (1H, s), 7.82-8.38 (3H, m, J=7.6 Hz, 1.5 Hz), 7.25 (1H, s), 6.80 (1H, s), 5.66 (4H, s), 2.82 (1H, m), 2.35-2.50 (4H, m), 1.99 (3H, s), 1.73 (6H, d, J=6.8 Hz), 1.36 (6H, d, J=6.8 Hz); $^{13}$C-NMR (101 MHz, DMSO-d$_6$) δ (ppm): 192.3, 177.8, 170.6, 162.1, 158.4, 157.1, 153.0, 152.3, 151.0, 148.9, 141.9, 140.4, 138.8, 137.8, 137.1, 136.7, 136.0, 128.5, 127.3, 126.0, 124.5, 123.5, 122.1, 120.4, 118.3, 116.2, 113.9, 108.3, 26.4, 26.1, 25.8, 24.2, 22.7, 20.4; MS (ESI) for (M+H)$^+$: 697.2.

Compound (B-2)

$^1$H-NMR (400 MHz, DMSO-d$_6$) δ (ppm): 12.77 (4H, s), 9.01 (2H, s), 7.81-8.23 (4H, m, J=7.5 Hz), 7.25 (2H, s), 6.81 (2H, s), 5.69 (2H, s), 2.56 (6H, s), 2.50 (2H, m, J=6.8 Hz), 1.41 (12H, d, J=6.8 Hz); $^{13}$C-NMR (101 MHz, DMSO-d$_6$) δ (ppm): 179.0, 171.6, 161.8, 159.4, 158.1, 151.2, 141.5, 138.6, 138.0, 134.7, 132.0, 130.4, 127.7, 126.8, 125.4, 123.1, 120.4, 118.8, 117.6, 103.9, 27.3, 23.8, 20.5; MS (ESI) for (M+H)$^+$: 875.2.

Example 3

The preparation of Compound (A-3) (Z)-8'-((4,7-dihydroxy-2-oxo-2H-chromen-3-yl)methylene)-1,1',6,6',7-pentahydroxy-5,5'-diisopropyl-3,3'-dimethyl-7'-oxo-7',8'-dihydro-[2,2'-binaphthalene]-8-carbaldehyde and Compound (B-3) (8Z,8'Z)-8,8'-bis((4,7-dihydroxy-2-oxo-2H-chromen-3-yl)methylene)-1,1',6,6'-tetrahydroxy-5,5'-diisopropyl-3,3'-dimethyl-[2,2'-binaphthalene]-7,7'(8H,8'H)-dione is shown below.

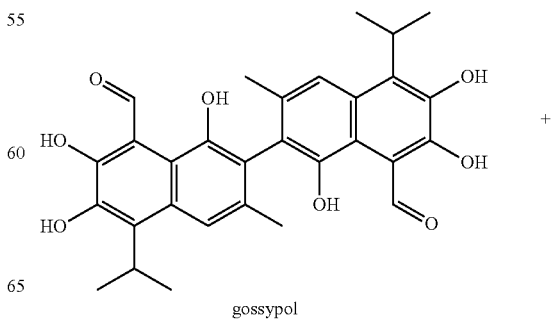

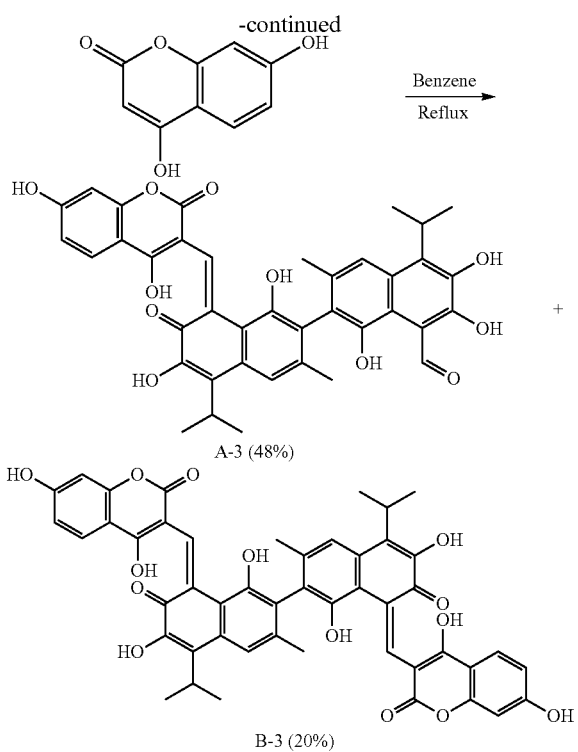

A-3 (48%)

B-3 (20%)

4.60 g (9 mmol) of 4,7-dihydroxycoumarin and 5.18 g (10.5 mmol) of gossypol were dissolved in 50 mL of benzene, placed in a round bottom flask, and 2 to 3 drops of N-methylmorpholine was slowly added dropwise under magnetic stirring. The mixture was then heated to 110° C. and reacted for 8 hours. When TLC indicated that the reaction was complete, reaction was stopped, the condensing unit was removed, and the reaction mixture was concentrated under reduced pressure. The concentrate was repeatedly eluted with 100 ml of eluent ethyl acetate-petroleum ether (2:1). Based on TCL tracking, the eluate containing the compound (A-3) and the compound (B-3) was collected separately. The resulting eluate was allowed to stand for crystallization and filtered, and the filtrate was recovered. The filter cake was washed with a small amount of ethanol to obtain the crude compounds (A-3) and (B-3). The crude product (A-3) was added to a reactor, and 25 ml of acetonitrile was added for recrystallization. After recrystallization, the resulted solution was filtered and dried to obtain 1.69 g of the compound (A-3), a yield of 40%. 0.70 g of the compound (B-3) was obtained by the same recrystallization method, a yield of 28%. The overall yield (mol %) is 68%.

Compound (A-3)

$^1$H-NMR (400 MHz, DMSO-d$_6$) δ (ppm): 12.31 (2H, s), 10.02 (1H, s), 8.43-8.67 (2H, m, J=7.5 Hz), 7.24 (1H, s), 6.77-6.92 (2H, m, J=7.4 Hz), 6.54 (1H, s), 5.75 (1H, s), 5.33 (4H, s), 2.79 (1H, m), 2.67 (3H, s), 2.54 (3H, s), 2.50 (1H, m), 1.82 (6H, d, J=6.8 Hz), 1.44 (6H, d, J=6.8 Hz); $^{13}$C-NMR (101 MHz, DMSO-d$_6$) δ (ppm): 190.1, 177.6, 170.2, 161.4, 158.3, 157.5, 157.7, 155.6, 155.1, 148.9, 143.7, 141.2, 137.4, 136.8, 135.6, 133.8, 132.1, 130.9, 127.1, 125.6, 123.1, 120.6, 118.3, 115.4, 112.9, 109.3, 108.0, 102.6, 101.3, 28.4, 27.1, 26.8, 25.2, 22.8, 21.2; MS (ESI) for (M+H)$^+$: 679.2.

Compound (B-3)

$^1$H-NMR (400 MHz, DMSO-d$_6$) δ (ppm): 12.42 (4H, s), 8.41 (2H, d, J=7.4 Hz), 7.21 (2H, s), 6.72-6.89 (2H, m, J=7.5 Hz), 6.52 (2H, s), 5.68 (4H, s), 2.54 (6H, s), 2.44 (2H, m, J=6.8 Hz), 1.50 (12H, d, J=6.8 Hz); $^{13}$C-NMR (101 MHz, DMSO-d$_6$) δ (ppm): 179.4, 171.2, 161.4, 159.3, 158.1, 157.9, 153.6, 140.1, 136.7, 136.0, 132.6, 130.1, 124.7, 123.1, 116.3, 111.9, 106.2, 101.7, 100.9, 25.8, 23.9, 20.9; MS (ESI) for (M+H)$^+$: 839.2.

Example 4

The preparation of Compound (A-4) (Z)-1,1',6,6',7-pentahydroxy-8'-((4-hydroxy-8-methoxy-2-oxo-2H-chromen-3-yl)methylene)-5,5'-diisopropyl-3,3'-dimethyl-7'-oxo-7',8'-dihydro-[2,2'-binaphthalene]-8-carbaldehyde and Compound (B-4) (8Z,8'Z)-1,1',6,6'-tetrahydroxy-8,8'-bis((4-hydroxy-8-methoxy-2-oxo-2H-chromen-3-yl)methylene)-5,5'-diisopropyl-3,3'-dimethyl-[2,2'-binaphthalene]-7,7'(8H,8'H)-dione is shown below.

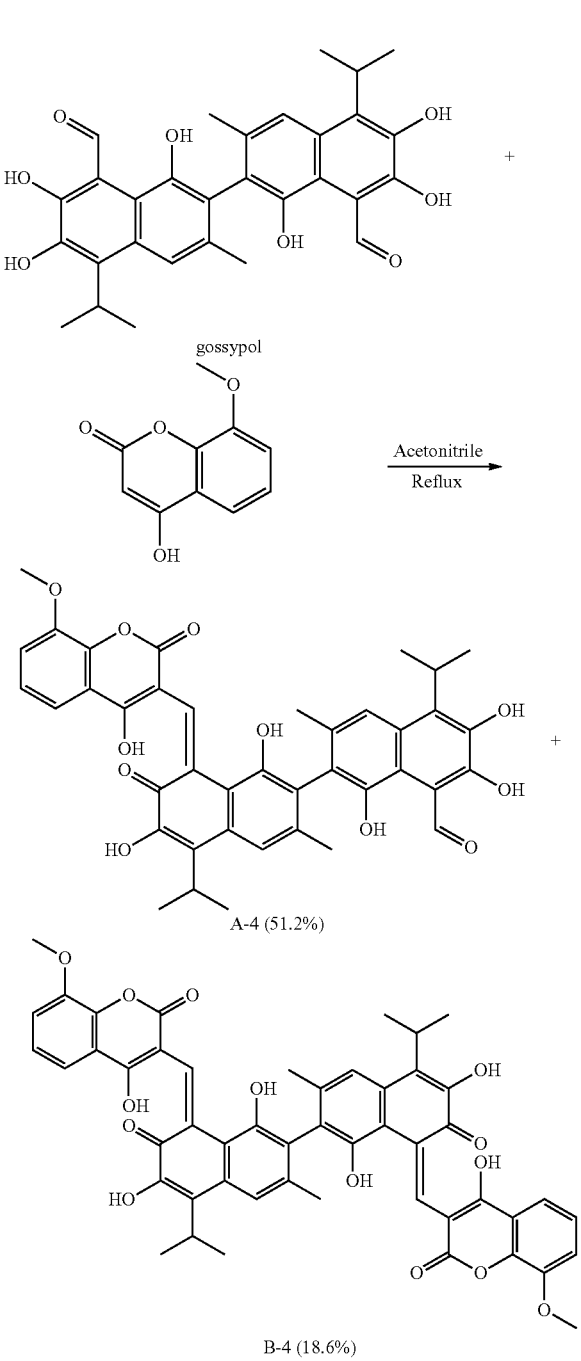

A-4 (51.2%)

B-4 (18.6%)

1.92 g (10 mmol) of 4-hydroxy-8-methoxycoumarin and 6.22 g (12 mmol) of gossypol were dissolved in 50 mL of acetonitrile, placed in a round bottom flask, and 2 to 3 drops of pyridine was slowly added dropwise under magnetic stirring. The mixture was then heated to 100° C. and reacted for 8 hours. When TLC indicated that the reaction was complete, reaction was stopped, the condensing unit was removed, and the reaction mixture was concentrated under reduced pressure. The concentrate was repeatedly eluted with 100 ml of eluent ethyl acetate-petroleum ether (2:1). Based on TCL tracking, the eluate containing the compound (A-4) and the compound (B-4) was collected separately. The resulting eluate was allowed to stand for crystallization and filtered, and the filtrate was recovered. The filter cake was washed with a small amount of ethanol to obtain the crude compounds (A-4) and (B-4). The crude product (A-4) was added to a reactor, and 25 ml of ethanol was added for recrystallization. After recrystallization, the resulted solution was filtered and dried to obtain 3.38 g of the compound (A-4). 0.46 g of the compound (B-4) was obtained by the same recrystallization method. The overall yield (mol %) is 69.8%.

Compound (A-4)

$^1$H-NMR (400 MHz, DMSO-$d_6$) δ (ppm): 12.25 (2H, s), 10.04 (1H, s), 7.66-8.21 (4H, m, J=7.5 Hz), 7.23 (1H, s), 6.63 (1H, s), 5.33 (4H, s), 3.85 (3H, s), 2.87 (1H, m), 2.72 (3H, s), 2.55 (3H, s), 2.48 (1H, m), 1.93 (6H, d, J=6.8 Hz), 1.56 (6H, d, J=6.8 Hz); $^{13}$C-NMR (101 MHz, DMSO-$d_6$) δ (ppm): 197.2, 177.6, 171.3, 161.8, 159.1, 156.9, 153.8, 147.7, 145.2, 143.6, 141.4, 138.8, 137.6, 134.1, 133.2, 131.5, 127.3, 126.0, 125.4, 123.1, 118.9, 119.2, 117.1, 116.3, 115.4, 115.9, 114.2, 107.8, 103.5, 56.8, 28.4, 27.5, 26.2 25.1 22.1, 21.2; MS (ESI) for (M+H)$^+$: 693.2.

Compound (B-4)

$^1$H-NMR (400 MHz, DMSO-$d_6$) δ (ppm): 12.23 (4H, s), 7.47-7.63 (6H, m, J=7.5 Hz), 7.25 (2H, s), 6.63 (2H, s), 5.53 (2H, s), 3.83 (6H, s), 2.79 (6H, s), 2.50 (2H, m, J=6.8 Hz), 1.62 (12H, d, J=6.8 Hz); $^{13}$C-NMR (101 MHz, DMSO-$d_6$) δ (ppm): 177.8, 171.4, 160.8, 158.2, 156.4, 146.2, 144.2, 141.4, 136.8, 136.2, 133.4, 127.3, 125.8, 125.4, 120.6, 119.4, 118.3, 117.1, 114.9, 102.6, 56.8, 27.8, 22.5, 20.2; MS (ESI) for (M+H)$^+$: 867.3.

Example 5

The preparation of (A-5) (Z)-1,1',6,6',7-pentahydroxy-5,5'-diisopropyl-3,3'-dimethyl-7'-oxo-8'-((4,5,7-trihydroxy-2-oxo-2H-chromen-3-yl)methylene)-7',8'-dihydro-[2,2'-binaphthalene]-8-carbaldehyde and compound (B-5) (8Z,8'Z)-1,1',6,6'-tetrahydroxy-5,5'-diisopropyl-3,3'-dimethyl-8,8'-bis((4,5,7-trihydroxy-2-oxo-2H-chromen-3-yl)methylene)-[2,2'-binaphthalene]-7,7'(8H,8'H)-dione is shown below.

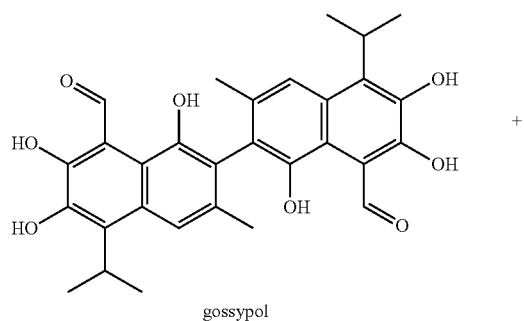

gossypol

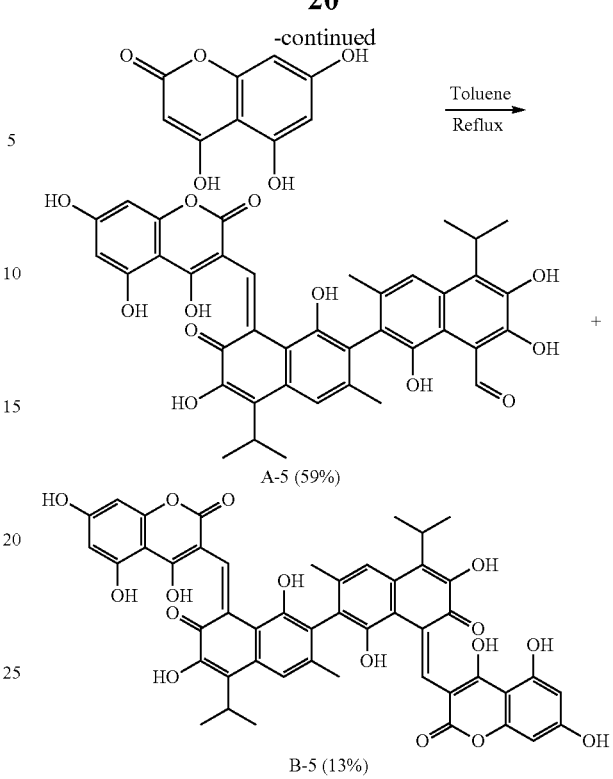

1.74 g (9 mmol) of 4,5,7-trihydroxycoumarin and 5.18 g (10 mmol) of gossypol were dissolved in 45 mL of toluene, placed in a round bottom flask, and 2 to 3 drops of pyridine was slowly added dropwise under magnetic stirring. The mixture was then heated to 120° C. and reacted for 8 hours. When TLC indicated that the reaction was complete, reaction was stopped, the condensing unit was removed, and the reaction mixture was concentrated under reduced pressure. The concentrate was repeatedly eluted with 100 ml of eluent ethyl acetate-petroleum ether (2:1). Based on TCL tracking, the eluate containing the compound (A-5) and the compound (B-5) was collected separately. The resulting eluate was allowed to stand for crystallization and filtered, and the filtrate was recovered. The filter cake was washed with a small amount of ethanol to obtain the crude compounds (A-5) and (B-5). The crude product (A-5) was added to a reactor, and 25 ml of ethanol was added for recrystallization. After recrystallization, the resulted solution was filtered and dried to obtain 2.20 g of the compound (A-5). 0.48 g of the compound (B-5) was obtained by the same recrystallization method. The overall yield (mol %) is 72%.

Compound (A-5)

$^1$H-NMR (400 MHz, DMSO-$d_6$) δ (ppm): 12.56 (2H, s), 10.11 (1H, s), 7.66 (1H, s), 7.23 (1H, s), 6.64 (1H, s), 6.42-6.58 (2H, m, J=7.4 Hz), 5.63 (4H, s), 5.35 (2H, s), 2.88 (1H, m), 2.69 (3H, s), 2.55 (3H, s), 2.42 (1H, m, J=6.8 Hz), 1.76 (6H, d, J=6.8 Hz), 1.41 (6H, d, J=6.8 Hz); $^{13}$C-NMR (101 MHz, DMSO-$d_6$) δ (ppm): 192.2, 179.6, 171.3, 161.8, 160.3, 159.2, 158.1 157.5, 156.2, 155.0, 149.7, 143.6, 142.4, 138.8, 137.9, 136.1, 134.7, 133.4, 129.3, 124.5, 123.5, 120.0, 118.6, 117.3, 115.2, 114.7, 103.5, 101.1, 99.6, 98.8, 26.4, 25.3, 23.1, 22.5, 21.5; MS (ESI) for (M+H)$^+$: 695.2.

Compound (B-5)

$^1$H-NMR (400 MHz, DMSO-$d_6$) δ (ppm): 12.60 (4H, s), 7.25 (2H, s), 6.86 (2H, s), 6.30-6.78 (4H, m, J=7.4 Hz), 5.65 (4H, s), 5.32 (2H, s), 2.57 (6H, s), 1.88 (2H, m, J=6.8 Hz), 1.56 (12H, d, J=6.8 Hz); $^{13}$C-NMR (101 MHz, DMSO-$d_6$) δ (ppm): 177.6, 171.3, 160.8, 158.1, 157.5, 151.4, 141.4, 136.8, 136.2, 133.4, 128.5, 126.1, 121.6, 120.1, 104.5, 101.3, 99.8, 97.6, 27.8, 23.5, 21.4; MS (ESI) for (M+H)$^+$: 871.2.

Example 6

The preparation of Compound (6-A) (Z)-1,1',6,6',7-pentahydroxy-8'-((4-hydroxy-5,7-dimethyl-2-oxo-2H-chromen-3-yl)methylene)-5,5'-diisopropyl-3,3'-dimethyl-7'-oxo-7',8'-dihydro-[2,2'-binaphthalene]-8-carbaldehyde and Compound (B-6) (8Z,8'Z)-1,1',6,6'-tetrahydroxy-8,8'-bis((4-hydroxy-5,7-dimethyl-2-oxo-2H-chromen-3-yl)methylene)-5,5'-diisopropyl-3,3'-dimethyl-[2,2'-binaphthalene]-7,7'(8H,8'H)-dione is shown below.

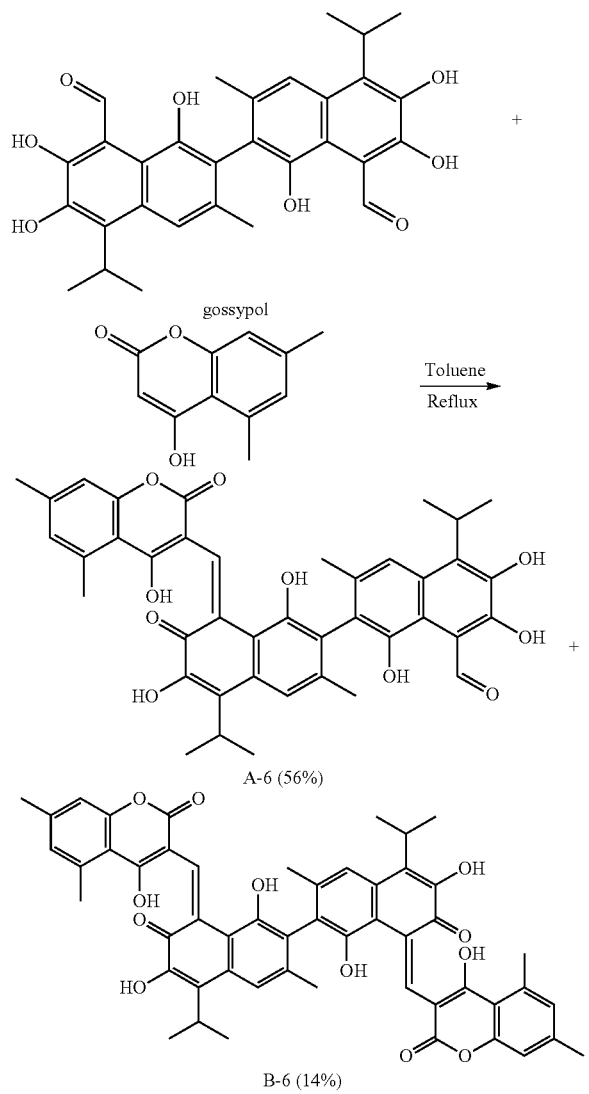

An appropriate amount of 1.90 g (10 mmol) of 4-hydroxy-5,7-dimethylcoumarin and 5.18 g (12 mmol) of gossypol were dissolved in 45 mL of toluene and placed in a round bottom flask. 3 drops of pyridine in the reaction solution, heated to 120° C., and reacted for 8 hours. TLC method was used to track the reaction to complete, stop heating, remove the condensing unit, and concentrate the reaction mixture under reduced pressure. The concentrate was repeatedly eluted with 100 ml of eluent ethyl acetate-petroleum ether (2:1) TCL Tracking Results The eluate was collected to enrich the compound (A-6) and the compound (B-6), respectively. The resulting eluate was allowed to stand for crystallization, and the filtrate was recovered. The filter cake was washed with a small amount of ethanol to obtain the crude compound (A-6) and (B-6). The crude product (A-6) was added to the reactor, and 25 ml of ethanol was added thereto to carry out recrystallization, and the mixture was dried by filtration to obtain 2.03 g of the compound (A-6), 0.51 g of the compound (B-6) For 70%.

1.90 g (10 mmol) of 4-hydroxy-5,7-dimethylcoumarin and 5.18 g (12 mmol) of gossypol were dissolved in 45 mL of toluene, placed in a round bottom flask, and 2 to 3 drops of pyridine was slowly added dropwise under magnetic stirring. The mixture was then heated to 120° C. and reacted for 8 hours. When TLC indicated that the reaction was complete, reaction was stopped, the condensing unit was removed, and the reaction mixture was concentrated under reduced pressure. The concentrate was repeatedly eluted with 100 ml of eluent ethyl acetate-petroleum ether (2:1). Based on TCL tracking, the eluate containing the compound (A-6) and the compound (B-6) was collected separately. The resulting eluate was allowed to stand for crystallization and filtered, and the filtrate was recovered. The filter cake was washed with a small amount of ethanol to obtain the crude compounds (A-6) and (B-6). The crude product (A-6) was added to a reactor, and 25 ml of ethanol was added for recrystallization. After recrystallization, the resulted solution was filtered and dried to obtain 2.03 g of the compound (A-6). 0.51 g of the compound (B-6) was obtained by the same recrystallization method. The overall yield (mol %) is 70%.

Compound (A-6)

$^1$H-NMR (400 MHz, DMSO-$d_6$) δ (ppm): 12.54 (2H, s), 10.03 (1H, s), 7.63 (1H, s), 7.29 (1H, s), 6.98-7.12 (2H, m, J=7.4 Hz), 6.76 (1H, s), 5.38 (4H, s), 2.88 (1H, m), 2.72 (3H, s), 2.64 (3H, s), 2.32-2.55 (7H, m, J=6.8 Hz), 1.83 (6H, d, J=6.8 Hz), 1.56 (6H, d J=6.8 Hz); $^{13}$C-NMR (101 MHz, DMSO-$d_6$) δ(ppm): 196.2, 177.6, 171.3, 161.8, 157.4, 156.9, 154.0, 149.9, 143.6, 139.4, 137.3, 136.2, 135.4, 134.5, 133.4, 132.4, 128.5, 127.1, 125.3, 123.1, 118.6, 117.3, 116.6, 114.5, 113.4, 112.5, 103.5, 28.1, 27.8, 25.0, 23.5, 21.8; MS (ESI) for (M+H)$^+$: 691.3.

Compound (B-6)

$^1$H-NMR (400 MHz, DMSO-$d_6$) δ (ppm): 12.65 (4H, s), 7.28 (2H, s), 6.93-7.21 (4H, m, J=1.5 Hz), 6.82 (2H, s), 5.43 (2H, s), 2.56 (6H, s), 2.49 (2H, m, J=6.8 Hz), 2.37 (6H, s), 2.26 (6H, s), 1.66 (12H, d, J=6.8 Hz); $^{13}$C-NMR (101 MHz, DMSO-$d_6$) δ (ppm): 177.6, 171.3, 161.6, 157.5, 157.9, 149.9, 141.4, 139.9, 138.2, 137.4, 136.2, 133.6, 127.1, 125.2, 123.1, 116.3, 28.8, 23.2, 21.7, 20.8; MS (ESI) for (M+H)$^+$: 863.3.

Example 7

The Anti-Tumor Activity Test of the Compounds of the Present Invention

The compounds of the present invention were subjected to tumor cell proliferation inhibition test, and conventional MTT method was used.

Cell lines: human hepatoma cells (HepG2), human lung cancer cells (A-549), human gastric cancer cells (SGC-7901). The culture medium was DMEM+15% NBS+double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Gossypol was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% $CO_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and $IC_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$ (unit: μmol/L)

| Compounds | $IC_{50}$ (μmol/L) | | |
|---|---|---|---|
| | HepG2 | A549 | SGC-7901 |
| A-1 | 10.72 ± 0.65 | 17.14 ± 0.72 | 21.27 ± 1.34 |
| A-2 | >100 | >100 | >100 |
| A-3 | 17.84 ± 0.95 | 26.72 ± 1.12 | 30.72 ± 1.31 |
| A-4 | 26.51 ± 1.02 | 43.37 ± 1.21 | 31.25 ± 1.33 |
| A-5 | >100 | >100 | 88.76 ± 3.02 |
| A-6 | 42.13 ± 1.04 | >100 | 32.60 ± 1.81 |
| B-1 | 15.16 ± 0.34 | 22.32 ± 0.90 | 26.88 ± 1.35 |
| B-2 | >100 | 68.47 ± 2.44 | >100 |
| B-3 | 16.73 ± 0.45 | 28.61 ± 0.64 | 33.23 ± 1.01 |
| B-4 | 22.36 ± 0.58 | 38.42 ± 0.79 | 39.99 ± 1.43 |
| B-5 | >100 | >100 | 54.32 ± 2.85 |
| B-6 | 58.58 ± 3.23 | >100 | >100 |
| Gossypol | 18.37 ± 0.71 | 26.32 ± 1.89 | 43.56 ± 2.03 |

The results show that the prepared gossypol-coumarin derivatives have good antitumor activities in the three cell lines tested. Compound (A-1) has the best antitumor activities. Compound (A-3), (B-1) and the like also have good antitumor activities in different cell lines. The above experimental results indicates that the compounds of the present invention have good antitumor activities and can be used for the study of antitumor agents.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound of formula A or formula B:

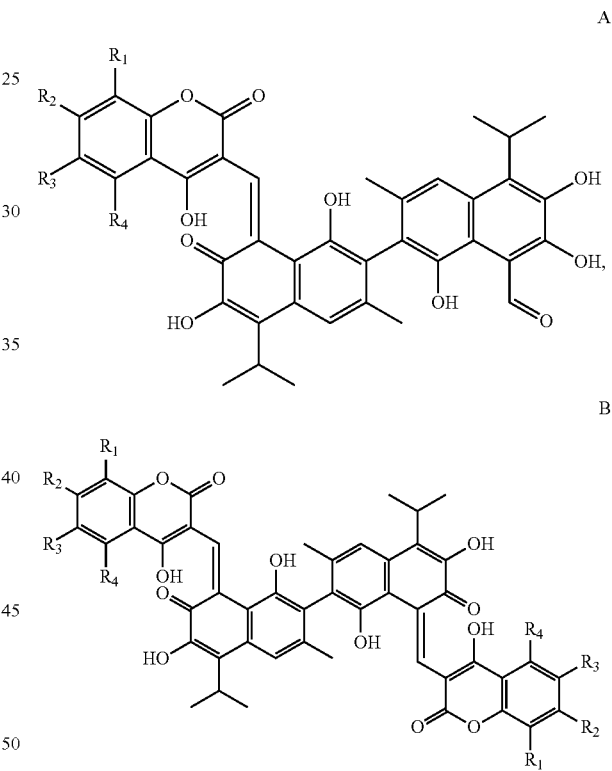

wherein $R_1$, $R_2$, $R_3$, and $R_4$ are independently hydrogen, hydroxyl, alkoxy, halogen, formyl, unsubstituted or substituted alkyl, or unsubstituted or substituted cycloalkyl.

2. The compound of claim 1, wherein $R_1$ is hydrogen, methoxy, hydroxyl, or halogen;

$R_2$ is methoxy, hydroxyl, or halogen;

$R_3$ is methyl, methoxy, hydroxyl, or halogen; and $R_4$ is hydrogen, formyl, hydroxyl, or halogen.

3. The compound of claim 1, wherein the compound is selected from the group consisting of:

(A-1) 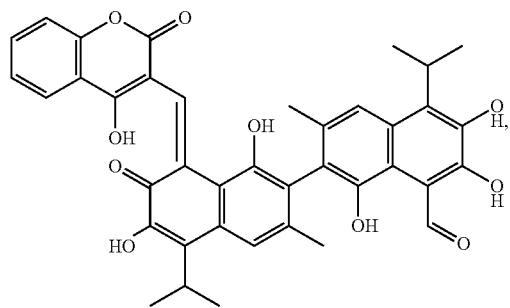
(A-2) 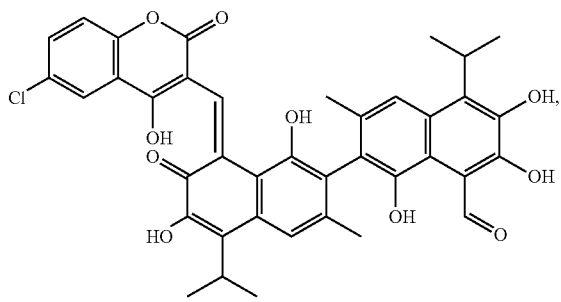
(A-3) 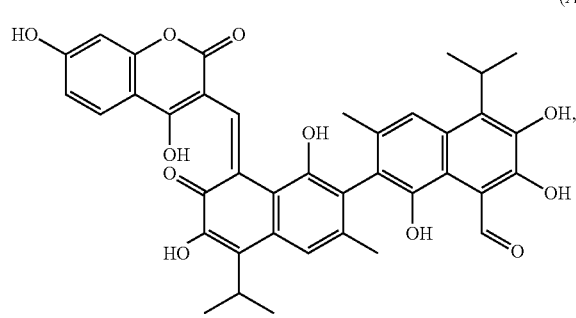
(A-4) 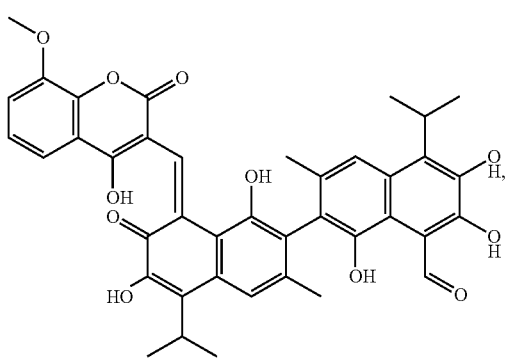
(A-5) 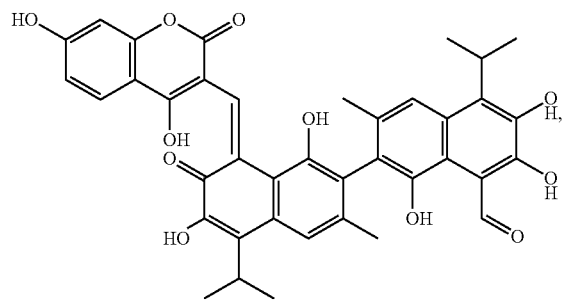
(A-6) 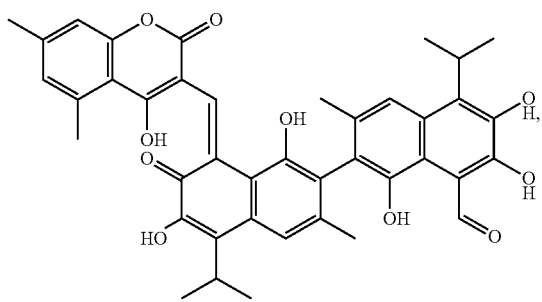
(B-1) 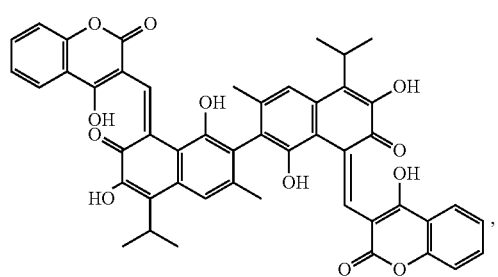
(B-2) 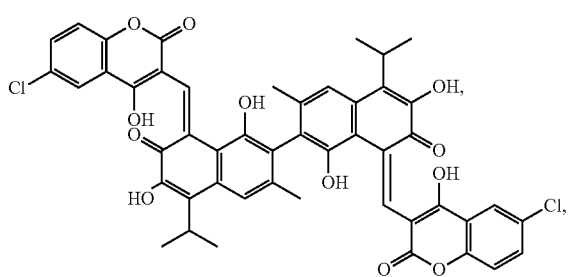

-continued
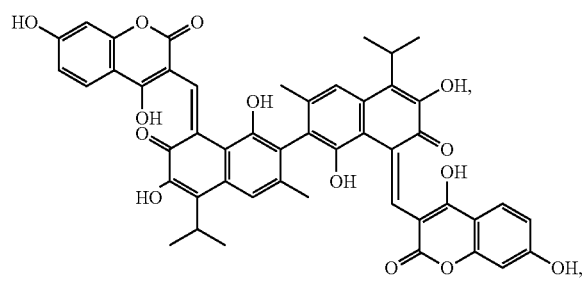
(B-3)
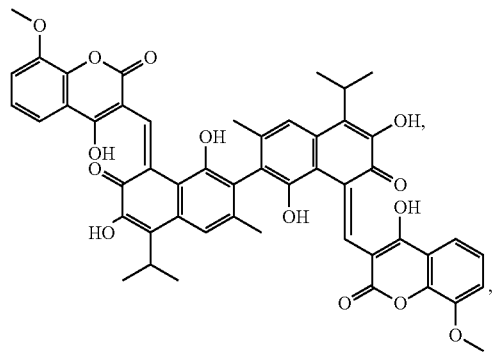
(B-4)
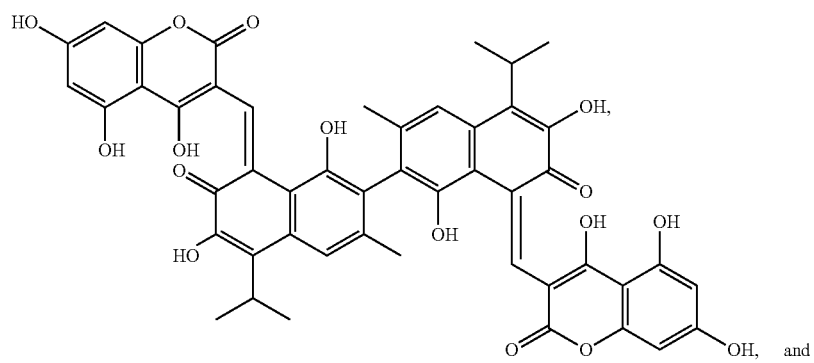
(B-5)
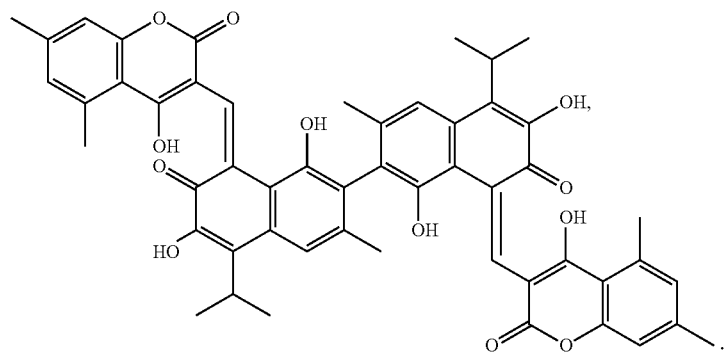
and
(B-6)
4. A method of preparing the compound of claim 1 comprising:
reacting a compound of formula C with a compound of formula D in an organic solvent with an organic base,
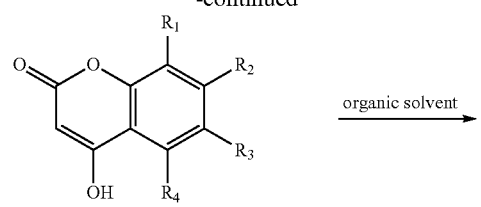
-continued
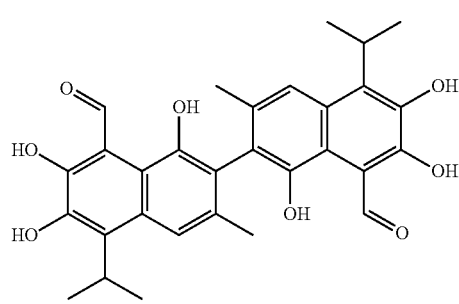
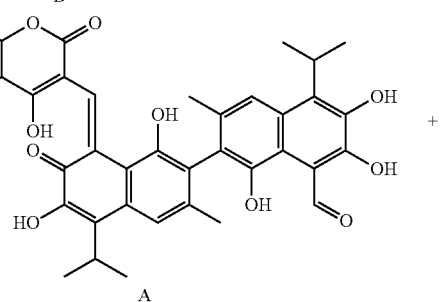

-continued

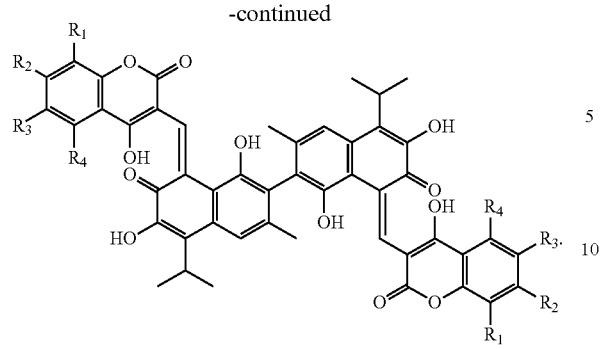

B

5. The method of claim 4, wherein the compound of formula C and the compound formula D are heated in the organic solvent for 6-9 hours.

6. The method of claim 4, wherein the organic solvent is acetonitrile, 1,4-dioxane, benzene, or toluene.

7. The method of claim 4, wherein the organic base is triethylamine, pyridine, or N-methylmorpholine.

8. The method of claim 4, further comprising:
    recrystallizing the compound of formula A or formula B in methanol, ethanol, or acetonitrile.

9. The method of claim 4, wherein a molar ratio of the compound of formula D to the compound of formula C is 1:0.5 to 1:1.5.

10. The method of claim 9, wherein the molar ratio of the compound of formula D to the compound of formula C is 1:1.2.

* * * * *